United States Patent [19]

Inukai et al.

[11] 4,246,280
[45] Jan. 20, 1981

[54] 20-ALKOXY-16-ALKYL-PROSTADIENOIC ACID DERIVATIVES

[75] Inventors: Noriyoshi Inukai; Masuo Murakami, both of Tokyo; Hidenori Iwamoto, Ageo; Isao Yanagisawa; Toshinari Tamura, both of Tokyo; Yoshio Ishii, Omiya; Kenichi Tomioka, Kitamoto, all of Japan; Tetsuya Shiozaki, deceased, late of Misato, Japan, by Hiroko Shiozaki, legal representative

[73] Assignee: Yamanouchi Pharmaceutical Co., Ltd., Tokyo, Japan

[21] Appl. No.: 16,070

[22] Filed: Feb. 28, 1979

Related U.S. Application Data

[63] Continuation of Ser. No. 861,459, Dec. 16, 1977, abandoned, which is a continuation of Ser. No. 702,889, Jul. 6, 1976, abandoned, which is a continuation-in-part of Ser. No. 640,497, Dec. 15, 1975, Pat. No. 4,055,589.

[30] Foreign Application Priority Data

Dec. 20, 1974 [JP] Japan ............................ 49/145617
Nov. 4, 1975 [JP] Japan ............................ 50/132295

[51] Int. Cl.$^3$ ............................................ A61K 31/557
[52] U.S. Cl. ................................. 424/305; 424/317
[58] Field of Search ................. 360/121; 562/503; 424/305, 317

[56] References Cited

U.S. PATENT DOCUMENTS 3,878,239  4/1975  Hayashi et al. ................. 562/503

Primary Examiner—Robert Gerstl
Attorney, Agent, or Firm—Burgess, Ryan and Wayne

[57] ABSTRACT

There are disclosed 20-alkoxy-16-alkyl-prostadienoic acid derivatives of the formula:

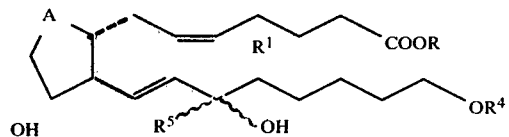

wherein A represents

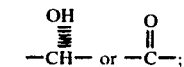

R and $R^5$, which may be the same or different, each represents a hydrogen atom or a lower alkyl group; and $R^1$ and $R^4$, which may be the same or different, each represents a lower alkyl group, and the pharmaceutically acceptable non-toxic salts thereof. These compounds have excellent pharmacological effects as prostaglandin $E_2$ and prostaglandin $F_{2\alpha}$.

4 Claims, No Drawings

20-ALKOXY-16-ALKYL-PROSTADIENOIC ACID DERIVATIVES

This is a continuation of application Ser. No. 861,459, filed Dec. 16, 1977, now abandoned, which is a continuation of U.S. Ser. No. 702,889, filed July 6, 1976, now abandoned, which is a continuation in part of U.S. Ser. No. 640,497, filed Dec. 15, 1975, now U.S. Pat. No. 4,055,589.

DETAILED DESCRIPTION OF THE INVENTION

The present invention relates to novel prostaglandin derivatives and more particularly it relates to 20-alkoxy-16-alkyl-prostadienoic acid derivatives of the formula I as follows:

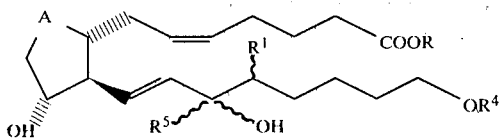

wherein A represents

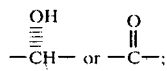

R and $R^5$, which may be the same or different, each represents a hydrogen atom or a lower alkyl group; and $R^1$ and $R^4$, which may be the same or different, each represents a lower alkyl group, and the pharmaceutically acceptable nontoxic salts thereof.

The compounds of this invention, that is, 20-alkoxy-16-alkyl prostadienoic acid derivatives shown by formula I can be prepared by removing the protective groups from the hydroxy group protected prostadienoic acid derivatives shown by formula II:

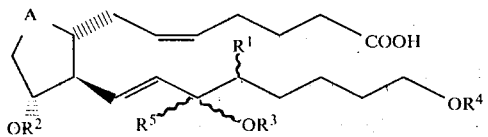

wherein A, $R^1$, $R^4$, and $R^5$ have the same meaning as in formula I and $R^2$ and $R^3$, which may be the same or different, each represents a hydrogen atom or a protective group for a hydroxy group, at least one of said $R^2$ and $R^3$ being the protective group for the hydroxy group and then esterifying if desired, the product.

Now in formula I, the lower alkyl group of R, $R^1$, $R^4$, and $R^5$ is a straight chain or branched chain alkyl group having 1-4 carbon atoms and suitable examples of the alkyl group are methyl group, ethyl group, propyl group, isopropyl group, butyl group, isobutyl group, etc.

Also, the dotted line bond to the cyclopentane ring means in alpha steric configuration, i.e., the substituent is positioned below the plane of the cyclopentane ring and the thick solid line bond means is beta steric configuration, i.e., the substituent is positioned above the plane of the cyclopentane ring. Furthermore, the wavy line bond at the side chain means in S steric configuration, R steric configuration, or the mixture thereof.

The compounds of formula I wherein R is a hydrogen atom form pharmacologically acceptable nontoxic salts. Typical examples of the salts are the salts of an alkali metal or an alkaline earth metal such as sodium, potassium, calcium, etc.; the ammonium salts; and the salts of organic amine such as tetramethyl ammonium, dimethylamine, piperidine, monoethanol amine, etc.

Conventionally known natural prostaglandins are unsaturated fatty acids having 20 carbon atoms and show various physiological activities. Among the natural prostaglandins, prostaglandin $E_2$ ($PGE_2$) shown by the formula

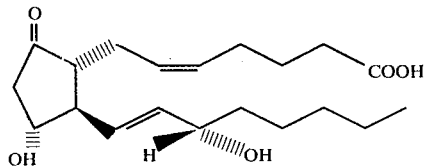

and prostaglandin $F_{2\alpha}$ ($PGF_{2\alpha}$) shown by the formula

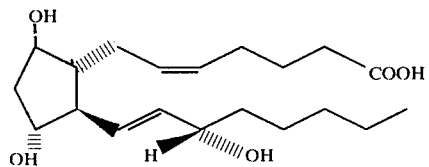

wherein the 15-position in S steric configuration are well known as the prostadienoic acid derivatives having various physiological activities. That is, prostaglandin $E_2$ and prostaglandin $F_{2\alpha}$ have such physiological effects as the contractile effect on smooth muscles of uterus, small intestines, etc., the hypotensive effect, and the hypertensive effect, the antilipolytic effect, the gastric antisecretory effect, the effect on central nervous system, the reducing effect of adhesiveness in the blood platelet, the antiaggregatory effect of the blood platelet, the preventive effect of the formation of thrombus, the proliferating effect of epidermis, the stimulating effect on cornification, etc. and thus they are useful for studying, preventing and reducing various diseases or undesirable physiological states in men and animals. For example, they are expected to be useful as agents for reducing or preventing the atonic uterine hemorrhage after abortion or delivery, the agent for the induction of labor, the agent for the interruption of pregnancy, the ovulation control agent, the hypotensive diuretic agent, the agent for curing thrombus, the antiasthmatic agent, the anti-ulcer agent, the anti-arteriosclerosic agent, etc.

However, it was reported that strong undesirable side-effect in particular, gastrointestinal side-effect, such as diarrhea was frequently observed in cases of administration of the natural prostaglandins (see, Lancet, Vol. II, 536(1971)).

Therefore, it is desirable to provide prostadienoic acid derivatives having higher physiological activities than the natural prostaglandins without undesirable side effects.

Various studies have been made for satisfying the requirement. For example, there are reported 16-alkyl-prostadienoic acid derivatives in which the 16-position of prostaglandin $E_2$ or $F_{2\alpha}$ is substituted by a lower alkyl group and the 20-alkoxy-prostadienoic acid derivative that the 20-position of prostaglandin E₂ or F$_{2\alpha}$ is substituted by a lower alkoxy group ("Journal of Organic Chemistry", 38(6), 1250 (1973) and Japanese Patent Application Laid Open No. 19,549/73). However, these prostadienoic acid derivatives are still inadequate for satisfying completely the aforesaid requirements.

On the other hand, the novel compounds of this invention, that is 20-alkoxy-16-alkyl-prostadienoic acid derivatives having the structure in which the 16-position of prostaglandin E₂ or F$_{2\alpha}$ is substituted with a lower alkyl group and the 20-position is substituted with a lower alkoxy group satisfy the aforesaid requirements. Namely, the compounds of this invention have excellent effects as prostaglandin E₂ and prostaglandin F$_{2\alpha}$, in particular a strong antiasthmatic effect upon oral administration, and show less undesirable side-effects such as diarrhea action. Thus, the compounds of this invention are useful as therapeutic agents.

As described above, the compounds of this invention are prepared from the hydroxy group-protected prostadienoic acid derivatives shown by Formula II and any groups which cause no change on the other parts of the compounds by the removal of the protecting group may be used as the protective groups for the hydroxy groups of R² and R³ in formula II and it is preferable that the protective group can be removed under mild condition. Examples of such protective groups are for example heterocyclic groups such as a tetrahydropyran-2-yl group, a tetrahydrothiopyran-2-yl group etc.; a trimethyl silyl group; an acyl group such as an acetyl group, a propionyl group, a benzoyl group, a p-phenylbenzoyl group a trifluoroacetyl group, etc.; a hydrocarbon group such as a tert-butyl group, a trityl group, etc.; and a carbonic acid ester residue such as a benzyloxycarbonyl group, an ethoxy carbonyl group, etc.

Suitable conditions are selected according to the nature of the protective group in removing the protective group of the hydroxy group.

That is, when the protective group for hydroxy group is a heterocyclic group such as a tetrahydropyran-2-yl group; a tert-butyl group; or a trityl group, the removal of the protective group may be conducted by treatment with acid.

Suitable acids used for the treatment are organic acids such as formic acid, acetic acid, propionic acid, oxalic acid, etc., and mineral acids such s hydrochloric acid, sulfuric acid, etc.

The acid treatment is carried out in a reaction solvent such as water, methanol, ethanol, tetrahydrofuran, dioxane or a mixture thereof. There is no limitation about the reaction temperature but the treatment is usually carried out at ambient temperature or under heating.

When the protective group for the hydroxy group is an acyl group such as an acetyl group, a propionyl group, a benzoyl group, a p-phenylbenzoyl group, and a trifluoroacetyl group, an acid or a base can be used for the removal of the protective group but the use of a base is preferable. Preferable examples of the acids are such mineral acids as hydrochloric acid and sulfuric acid and preferable examples of the base are sodium hydroxide, potassium hydroxide, sodium carbonate and potassium carbonate. As the reaction solvent, water, methanol, ethanol, tetrahydrofuran, dioxa or a mixture thereof can be used.

When the protective group for the hydroxy group is a trimethylsilyl group, the removal of the protective group is carried out by contacting the compound with water. The water used may contain an acid or a base. Also, a water-containing organic solvent, such as water-containing tetrahydrofuran, water-containing dioxane, water-containing methanol, and water-containing ethanol may be used in place of water.

Also, when the protective group for the hydroxy group is a carbonic acid ester residue such as benzyloxycarbonyl group, the removal of the protective group is carried out by treating with hydrogen bromide in acetic acid or by subjecting to a catalytic reduction.

Then, if desired, the product thus obtained is esterified in a known manner. For example, the esterification may be carried out by treating the product with an equimolar amount or slightly excessive amount of a diazo lower alkane such as diazomethane, diazoethane in an inert organic solvent such as dioxane, ether, etc., under cooling.

In addition, in the case of producing the compound of this invention, the starting material of formula II wherein A is

is prepared by oxidizing the compound of formula II wherein A is

the oxidation product (A is

in formula II) may be used in subsequent reaction without isolating.

After the reaction is over, the subject compound is isolated or purified in a known manner. For example, it would be suitable to isolate or purify the compound of formula I by extraction with an organic solvent, column chromatography, etc.

In addition, the starting material of formula II is a novel compound and the production of compound II is illustrated in the following reference examples.

Typical examples of the compounds of this invention are as follows:

9α,11α,15-Trihydroxy-20-methoxy-16-methyl-5-(cis)-13(trans)-prostadienoic acid,

9α,11α,15(R)-Trihydroxy-20-methoxy-16-methyl-5(cis)-13(trans)-prostadienoic acid, 9α,11α,15-Trihydroxy-20-methoxy-16-methyl-5(cis)-13(trans)-prostadienoic acid, 9α,11α,15-Trihydroxy-20-methoxy-16-methyl-5(cis)-13(trans)-prostadienoic acid, 9α,11α,15-Trihydroxy-20-methoxy-16-methyl-5(cis)-13(trans)-prostadienoic acid, 9α,11α,15-Trihydroxy-20-methoxy-16-methyl-5(cis)-13(trans)-prostadienoic acid, 11α,15(S)-Dihydroxy-20-methoxy-16-methyl-9-oxo-5(cis)-13(trans)-prostadienoic acid, 11α,15(R)-Dihydroxy-20-methoxy-16-methyl-9-oxo-5(cis)-13(trans)-prostadienoic acid, 11α,15(S)-Dihydroxy-20-methoxy-16(R)-methyl-9-oxo-5(cis)-13(trans)prostadienoic acid, 11α,15-Dihydroxy-20-methoxy-16-methyl-9-oxo-5(cis)-13(trans)prostadienoic acid, 11α,15-Dihydroxy-20-methoxy-16-methyl-9-oxo-5(cis)-13(trans)prostadienoic acid, 11α,15-Dihydroxy-20-methoxy-16-methyl-9-oxo-5(cis)-13(trans)prostadienoic acid, 11α,15-Dihydroxy-20-methoxy-16-methyl-9-oxo-5(cis)-13(trans)-prostadienoic acid methyl ester, 11α,15(R)-Dihydroxy-20-methoxy-16-methyl-9-oxo-5(cis)-13(trans)-prostadienoic acid methyl ester, 11α,15-Dihydroxy-20-methoxy-16-methyl-9-oxo-5(cis)-13(trans)prostadienoic acid ethyl ester 11α,15-Dihydroxy-20-methoxy-15,16-dimethyl-9-oxo-5(cis)-13(trans)-prostadienoic acid 11α,15-Dihydroxy-20-methoxy-15,16-dimethyl-9-oxo-5(cis)-13(trans)prostadienoic acid methyl ester.

The novel compounds of this invention are used for various medicinal preparations containing the compound or the salt thereof and are administered in various ways, for example, intravenously, orally, or locally (including aerosol) in the vagina or nose. The most important use of the compound of this invention is perhaps an antiasthmatic agent by oral administration from the view point of its physiological activity. The dosage form suitable from this purpose is tablets, capsules, powders and syrups. The dose of clinical administration of the compounds of this invention is 0.05–5 mg/day.

The pharmacological activities of the compound of this invention was tested in comparison with those of natural prostaglandin, the 16-methyl derivative thereof, and the 20-methoxy derivative thereof. The results are shown in Table I.

EXPERIMENTAL PROCEDURE

I. Antiasthmatic effect (i) Aerosol

Guinea-pigs were placed in a chamber and sprayed for 10 sec with an aerosol of histamine solution (0.1%) and onset of sneezing was recorded and animals with control time of 70–100 sec were selected. These animals were sprayed for 15 sec with an aerosol of test compounds. After 45 sec, sprayed histamine and observed for 3 min it was. If an animal did not show sneezing within 3 min, decided this animal was protected. The percent of animals protected was determined.

(ii) Oral

Guinea-pigs were sprayed for 10 sec with histamine 30 min after oral administration of test compounds and observed for 3 min. The percent of aminals protected was determined.

II. Diaarrhea-producing effect

Test compounds were administered orally to guinea-pigs. The appearance of diarrhea (loose or watery feces) at 2hr, 3hr, 4hr, 5hr and next morning was noted. The percent of animals exhibiting diarrhea was determined.

III. Effect on air-way resistance

The air-way resistance of the guinea-pig lung was determined by the method of Konzett and Rössler (Arch. exp. Path. Pharmak., 195, 71–74(1940)). The bronchorelaxing activity of prostaglandins were expressed in terms of protective effect against bronchoconstriction elicited by intravenous injection of histamine (3 μg/kg). Histamine was injected 30 min after intraduodenal administration of test compound to urethane anesthetized and artificially ventilated guinea-pigs.

TABLE 1

| Test material | Antiasthmatic effect | | (A) (b) | b/a | (B) ED$_{50}$μg/k |
|---|---|---|---|---|---|
| | Aerosol ED$_{50}$μg/ml | Oral (a) ED$_{50}$μg/kg | | | |
| Known compound Prostaglandin E$_2$ (PGE$_2$) | 0.15 | >800 | — | — | >800 |
| 11α,15-dihydroxy-20-methoxy-9-oxo-5(cis)-13(trans)prostadienoic acid (20-methoxy-PGE$_2$) | 0.15 | >800 | — | — | — |
| 11α,15-dihydroxy-16(R)-methyl-9-oxo-5(cis)-13(trans)prostadienoic acid (16-methyl-PGE$_2$) | 0.011 | 17.5 | 25 | 1.43 | — |
| 11α,15-dihydroxy-16-methyl-9-oxo-5(cis)-13(trans)prostadienoic acid (16-methyl-PGE$_2$) | 0.009 | 25 | 100 | 4.0 | — |
| Compound of this invention 11α,15-dihydroxy-20-methoxy-16-methyl-9-oxo-5(cis)-13(trans)prostadienoic acid showing $[\alpha]_D^{25}$ −51.5° (c = 0.78, methanol) Example 3 (20-methoxy-16-methyl-PGE$_2$) | 0.037 | 9.8 | 120 | 12.2 | 13.5 |
| 11α,15-dihydroxy-20-methoxy-16(S)-methyl-9-oxo-5(cis)-13(trans)prostadienoic acid showing $[\alpha]_D^{25}$ −65.0° (c = 0.5, chloroform) Example 6 (20-methoxy-16-methyl-PGE$_2$) | — | 710 | 140 | 20.0 | — |
| 11α,15-dihydroxy-20-methoxy-16(S)-methyl-9-oxo-5(cis)-13(trans)prostadienoic acid methyl ester | — | 16.0 | 145 | 9.06 | — |

TABLE 1-continued

| Test material | Antiasthmatic effect | | | | |
|---|---|---|---|---|---|
| | Aerosol ED$_{50}\mu$g/ml | Oral (a) ED$_{50}\mu$g/kg | (A) (b) | b/a | (B) ED$_{50}\mu$g/k |
| showing $[\alpha]_D^{25}$ −58.0° (c = 0.6, chloroform) Example 7 (20-methoxy-16-methyl-PGE$_2$ methyl ester) | | | | | |
| 11$\alpha$,15-dihydroxy-20-methoxy-16-methyl-9-oxo-5(cis)-13(trans)prostadienoic acid methyl ester showing $[\alpha]_D^{25}$ −66.4° (c = 0.4, chloroform) Example 7 (20-methoxy-16-methyl-PGE$_2$ methyl ester) | — | 5.3 | 51 | 9.62 | — |

(A): Diarrhea-producing effect
(B): Effect on air-way resistance

It is clear from the results shown in Table 1, that 20-methoxy-16-methyl-PGE$_2$ and the methyl ester thereof, which are the compounds within the scope of this invention, show strong antiasthmatic effect in both aerosol administration and oral administration. In particular, PGE$_2$ and 20-methoxy-PGE$_2$, which are known compounds, show no antiasthmatic effect upon oral administration and 16-methyl-PGE$_2$ shows some effect, while 20-methoxy-16-methyl-PGE$_2$ shows quite strong antiasthmatic effect. The fact that 20-methoxy-16-methyl-PGE$_2$ and the methyl ester thereof show a remarkable antiasthmatic effect upon oral administration is further supported by the fact that they show a strong reduction of air-way resistance in intraduodenal administration.

Also, 20-methoxy-16-methyl-PGE$_2$ and the methyl ester thereof show less diarrhea action in oral administration than 16-methyl-PGE$_2$.

Furthermore, the fact that the value of b/a is largest in 20-methoxy-16-methyl-PGE$_2$ and the methyl ester thereof as shown in Table I supports the conclusion that 20-methoxy-16-methyl-PGE$_2$ and the methyl ester thereof have a quite selective antiasthmatic activity.

Accordingly, it is clear that 20-methoxy-16-methyl-PGE$_2$ and the methyl ester thereof which are the compounds of this invention, are the prostadienoic acid derivatives having higher physiological activities and less side-effects than natural prostaglandin which is the mother body of the compounds of this invention. In particular, since the compounds of this invention have strong antiasthmatic activity upon oral administration, and show less diarrhea action which is one of the side-effects, they are selective antiasthmatic agents.

REFERENCE EXAMPLE 1

(a) To 60 ml. of anhydrous dimethoxyethane was added 685 mg. of 50% oily sodium hydride under a nitrogen stream and after adding dropwise to the mixture a solution of 3.8 g. of dimethyl-(7-methoxy-3-methyl-2-oxo)heptylphosphonate in 40 ml. of anhydrous dimethoxyethane, the resultant mixture was stirred for 2 hours at room temperature. Then, a solution of 5.5 g. of 4$\beta$-formyl-2-oxo-5$\alpha$-p-phenylbenzoyloxy-3a$\alpha$,4$\alpha$,5$\beta$,6a$\alpha$-hexahydro-2H-cyclopenta[b]furan in 150 ml. of anhydrous dimethoxyethane was added dropwise to the mixture and then the resultant mixture was stirred for 90 minutes at room temperature.

After the reaction was over, the reaction mixture was neutralized with dry ice powder and 200 ml of water was added thereto and then the mixture was saturated with sodium chloride. The resultant mixture was extracted 4 times each time with 50 ml. of methylene chloride. The extracts were combined, washed with water, dried over anhydrous magnesium sulfate, and concentrated under a reduced pressure to provide 9.2 g. of a crude oily product of 4$\beta$-[8-methoxy-4-methyl-3-oxo-1-(trans)octenyl]-2-oxo-5$\alpha$-p-phenylbenzoyloxy-3a$\alpha$,4$\alpha$,5$\beta$,6a$\alpha$-hexahydro-2H-cyclopenta[b]furan.

(b) After adding 3.78 g. of sodium borohydride and 5.57 g. of zinc chloride to 250 ml. of anhydrous ether followed by stirring for 90 minutes at room temperature, a solution of 9.2 g. of crude 4$\beta$-[8-methoxy-4-methyl-3-oxo-1-(trans)octenyl]-2-oxo-5$\alpha$-p-phenylbenzoyloxy-3a$\alpha$,4$\alpha$,5$\beta$,6a$\alpha$-hexahydro-2H-cyclopenta[b]furan in 100 ml. of anhydrous tetrahydrofuran was added dropwise to the mixture, and then the resultant mixture was stirred for 2 hours at room temperature.

After the reaction was over, the reduction mixture was neutralized with a dry ice powder and 150 ml. of water was added thereto and then the resultant mixture was extracted three times each time with 50 ml. of ether. The extraction were combined, washed with water, dried over anhydrous magnesium sulfate, and concentrated under a reduced pressure to provide 7.7 g. of the crude product. The crude product was applied to a silica gel column chromatography and then developed using a mixture of n-hexane and ethyl acetate as eluting solution to provide 2.0 g. of 4$\beta$-[3-hydroxy-8-methoxy-4-methyl-1-transoctenyl]-2-oxo-5$\alpha$-p-phenylbenzoyloxy-3a$\alpha$,4$\alpha$,5$\beta$,6a$\alpha$-hexahydro-2H-cyclopenta[b]furan showing $[\alpha]_D^{25}$-74.1° (c=2.37, chloroform) and 1.3 g. of 4$\beta$-[3-hydroxy-8-methoxy-4-methyl-1-(trans)octenyl]-2-oxo-5$\alpha$-p-phenylbenzoyloxy-3a$\alpha$,4$\alpha$,5$\beta$,-6a$\alpha$-hexahydro-2H-cyclopenta[b]furan showing $[\alpha]_D^{25}$-91.3° (c=2.04, chloroform).

(c) In 150 ml. of dry methanol was dissolved 2.0 g. of 4$\beta$-[3(S)-hydroxy-8-methoxy-4-methyl-1-(trans)octenyl]-2-oxo-5$\alpha$-p-phenylbenzoyloxy-3a$\alpha$,4$\alpha$,5$\beta$,6a$\alpha$-hexahydro-2H-cyclopenta[b]furan in a nitrogen stream and after adding 300 mg. of potassium carbonate to the solution, the mixture was stirred for 3 hours at room temperature and then for one hour at 40° C. The mixture was neutralized with acetic acid and then methanol was distilled off under a reduced pressure. To the residue containing crystals thus obtained was added 100 ml. of water and after saturating the mixture with sodium chloride, the resultant mixture was extracted thrice each with 50 ml. of ethyl acetate. The extracts were combined, washed with a saturated aqueous of sodium chloride solution, dried over anhydrous magnesium sulfate, and concentrated under a reduced pressure to provide the crude product. The product was applied to a silica gel column chromatography and then developed using a mixture of methylene chloride and ethyl acetate as eluting solution to provide 1.2879 g. of 4β-[3(S)-hydroxy-8-methoxy-4-methyl-1-(trans)octenyl]-5α-hydroxy-2-oxo-3aα,4α,5β,6aα-hexahydro-2H-cyclopenta[b]furan showing $[\alpha]_D^{25}$ +2.43 (c=1.85, chloroform).

(d) In 50 ml. of anhydrous methylene chloride was dissolved 1.2879 g. of 4β-[3-hydroxy-8-methoxy-4-methyl-1-(trans)octenyl]-5α-hydroxy-2-oxo-3aα,-4α,5β,6aα-hexahydro-2H-cyclopenta[b]furan and after adding to the solution 1.025 g. of 2,3-dihydropyran and further 12 mg. of p-toluene sulfonic acid monohydrate followed by stirring for 30 minutes at room temperature, 30 ml. of methylene chloride was added to the mixture. Then, the methylene chloride layer formed was recovered, washed with a diluted aqueous solution sodium bicarbonate solution and then water, dried over anhydrous magnesium sulfate and concentrated under a reduced pressure to provide 1.9576 g. of crude 4β-[8-methoxy-4-methyl-3(S)-(tetrahydropyran-2-yloxy)-1-(trans)octenyl]-2-oxo-5α-(tetrahydropyran-2-yloxy)-3aα,4α,5β,6aα-hexahydro-2H-cyclopenta[b]furan.

(e) In 80 ml. of anhydrous toluene was dissolved 1.9576 g. of crude 4β-[8methoxy-4-methyl-3(S)-(tetrahydropyran-2-yloxy)-1-(trans)octenyl]-2-oxo-5α-(tetrahydropyran-2-yloxy)-3aα,4α,5β,6aα-hexahydro-2H-cyclopenta[b]furan in nitrogen stream and the solution was cooled to −60° C. by dry-ice acetone. Then, 13.0 ml of a toluene solution containing 1.27 g. of diisobutylaluminum hydride was added dropwise to the solution under a stream of nitrogen and the mixture was stirred for 30 minutes at the same temperature.

Then, after adding to the reaction mixture 15 ml. of ethyl acetate, 7 ml. of methanol, and 5 ml. of water successively, 70 ml. of water was further added to the mixture, whereby white precipitates were formed. After filtering off the precipitates, the filtrate was separated into an aqueous layer and an organic layer. The aqueous layer was extracted three times, each time with 50 ml. of benzene and the extracts and the organic layer were combined, washed with a saturated aqueous sodium chloride solution and then water, dried over anhydrous magnesium sulfate, and concentrated under a reduced pressure at a temperature below room temperature to provide 2.0463 g. of 4β-[8-methoxy-4-methyl-3-(tetrahydropyran-2-yloxy)-1-(trans)octenyl]-2-hydroxy-5α-(tetrahydropyran-2-yloxy)-3aα,4α,5β,6aα-hexahydro-2H-cyclopenta[b]furan.

(f) To 935 ml. of 50% oily sodium hydride was added 25 ml. anhydrous dimethyl sulfoxide in nitrogen stream and the mixture was stirred under heating to 70°–75° C. for about one hour until the evolution of hydrogen gas ceased. Then, the reaction mixture was cooled to room temperature and then after adding thereto 4.5 g. of 4-carboxybutyltriphenyl phosphonium bromide, a solution of 2.0463 g. of 4β-[8-methoxy-4-methoxy-3-(tetrahydropyran-2-yloxy)-1-(trans)octenyl]-2-hydroxy-5α-(tetrahydropyran-2-yloxy)-3aα,4α,5β,6aα-hexahydro-2H-cyclopenta[b]furan in 15 ml. of anhydrous dimethyl sulfoxide was added to the mixture followed by stirring for one hour at room temperature.

After the reaction was over, the reaction mixture was neutralized with a dry ice powder and then a mixture of 150 ml. of ethyl acetate and 70 ml. of ether saturated with dry ice and ice water were added to the reaction mixture and then shaken well. The resultant mixture formed was separated into an aqueous layer and an organic layer and the aqueous layer was extracted three times each time with 30 ml. of ethyl acetate. The extracts were combined with the organic layer and the resultant mixture was washed with ice-water, dried over anhydrous magnesium sulfate, and concentrated under a reduced pressure to provide 3.4 g. of crude 9α-hydroxy-20-methoxy-16-methyl-11α,15-bis(tetrahydropyran-2-yloxy)-5(cis)-13(trans)prostadienoic acid.

The crude product was applied to a silica gel column chromatography and developed using a mixture of ethyl acetate and n-hexane as eluting solution to provide 1.4998 g. of the oily product showing $[\alpha]_D^{25}$+1.32° (c=1.14, chloroform).

(g) In 5 ml. of ether was dissolved 153.8 mg. of 9α-hydroxy-20-methoxy-16-methyl-11α,15-bis(tetrahydropyran-2-yloxy)-5(cis)-13(trans)prostadienoic acid and the solution was cooled to 0° C. to −5° C. Then, 5.0 ml. of the solution (which was prepared in portion of 2.0 g. of anhydrous chromic acid, 9.65 g. of manganese sulfate hydrate, 2.13 ml. of concentrated sulfuric acid and water to make the whole volume 50 ml. and precooled to 0° C. to −5° C.) was added to the mixture and stirred for 3 hours at the same temperature.

After the reaction was over, 10 ml. of water was added to the reaction mixture and the mixture was extracted three times each time with 30 ml. of ether. The extracts were combined, washed with water, dried over anhydrous magnesium sulfate, and concentrated under a reduced pressure to provide 143.5 mg. of 20-methoxy-16-methyl-9-oxo-11α,15(S)-bis(tetrahydropyran-2-yloxy)-5-(cis)-13(trans)prostadienoic acid.

REFERENCE EXAMPLE 2

(a) In 120 ml. of dry methanol was dissolved 1.3 g. of 4β-[3-hydroxy-8-metoxy-4-methyl-1-(trans)octenyl]-2-oxo-5α-p-phenylbenzoyloxy-3aα,4α,5β,6aα-hexahydro-2H-cyclopenta[b]furan and after adding thereto 196 mg. of potassium carbonate, the mixture was stirred for 3 hours at room temperature and then for 1 hour at 40° C. under a stream of nitrogen. The mixture was neutralized with acetic acid and the methanol was distilled off under a reduced pressure. The residue containing crystals thus obtained was mixed with 100 ml. of water and then after saturating the mixture with sodium chloride, the resultant mixture was extracted three times, each time with 50 ml. of ethyl acetate. The extracts were combined, washed with saturated aqueous sodium chloride solution, dried over anhydrous magnesium sulfate, and concentrated under a reduced pressure to provide the crude product.

The crude product was applied to a silica gel column chromatography and developed using a mixture of methylene chloride and ethyl acetate as eluting solution to provide 0.6947 g. of 4β-[3(R)-hydroxy-8-methoxy-4-methyl-1-(trans)octenyl]-5α-hydroxy-2-oxo 3aα,4α,5β,-6aα-hexahydro-2H-cyclopenta[b]furan.

$\alpha_D^{25}$ −20.5° (c=1.87, chloroform).

(b) In 30 ml. of anhydrous methylene chloride was dissolved 0.6947 g. of 4β-[3-hydroxy-8-methoxy-4-methyl-1-(trans)octenyl]. 5α-hydroxy-2-oxo-3aα, 4α,5β,6aα-hexahydro-2H-cyclopenta[b]furan. Then, 0.561 g. of 2,3-dihydropyran and 6.3 mg. of p-toluene-sulfonic acid monohydrate were added to the solution and after stirring the mixture for 30 minutes at room temperature, 20 ml. of methylene chloride was further added to the mixture. Then, the methylene chloride layer was recovered, washed with diluted aqueous sodium bicarbonate solution and then water, dried over anhydrous magnesium sulfate, and concentrated under a reduced pressure to provide 1.0693 g. of crude 4β-[8-metoxy-4-methyl-3-

(tetrahydropyran-2-yloxy)-1-(trans)octenyl]-2-oxo-5α-(tetrahydropyran-2-yloxy)-3aα,4α,5β,6aα-hexahydro-2H-cyclopenta[b]furan.

(c) In 50 ml. of anhydrous toluene was dissolved 0.0693 g. of 4β-[8-methoxy-4-methyl-3(R)-(tetrahydropyran-2-yloxy)-1-(trans)octenyl]-2-oxo-5α-(tetrahydropyran-2-yloxy)-3aα,4α,5β,6aα-hexahydro-2H-cyclopenta[b] furan under a nitrogen stream and after cooling the solution to −60° C., 7.1 ml. of a toluene solution containing 695 mg of diisobutylaluminum hydride was added dropwise to the solution under a stream of nitrogen and the mixture was stirred for 30 minutes at the same temperature.

Then, to the reaction mixture was added 15 ml. of ethyl acetate, 7 ml. of methanol, and then 5 ml. of water successively at the same temperature and then 50 ml. of water was added to the mixture at room temperature, whereby white precipitates were formed. The precipitates were filtered off and the filtrate was separated into an aqueous layer and an organic layer. The aqueous layer was extracted three times, each time with 50 ml. of benzene and the extracts were combined with the organic layer. The mixture was washed with saturated aqueous sodium chloride solution and then water, dried over anhydrous magnesium sulfate, and concentrated under a reduced pressure at temperatures below room temperature to provide 0.9791 g. of 4β-[8-methoxy-4-methyl-3-(tetrahydropyran-2-yloxy)-1-(trans)octenyl]-2-hydroxy-5α-(tetrahydropyran-2-yloxy)-3aα,4α,5β,-6aα-hexahydro-2H-cyclopenta[b]furan.

(d) To 468 mg. of 50% oily sodium hydride was added 15 ml. of anhydrous dimethylsulfoxide under a stream of nitrogen and the mixture was stirred under heating to 70°–75° C. for about one hour until the evolution of hydrogen gas ceased. Then, the reaction mixture was cooled to room temperature and 2.25 g. of 4-carboxybutyltriphenyl phosphonium bromide was added to the mixture. Thereafter, a solution of 0.9791 g. of 4β-[8-methoxy-4-methyl-3-(tetrahydropyran-2-yloxy)-1-(trans)octenyl]-2-hydroxy-5α-(tetrahydropyran-2-yloxy)-3aα,4α,5β,6aα-hexahydro-2H-cyclopenta-[b]furan in 10 ml. of anhydrous dimethylsulfoxide was further added to the mixture and the resultant mixture was stirred for one hour at room temperature.

After the reaction was over, the reaction mixture was neutralized with dry ice powder and a mixture of 150 ml. of ethyl acetate and 70 ml. of ether saturated with dry ice and cold water were added to the mixture and then shaken well. The resultant mixture was separated into an aqueous layer and an organic layer. The aqueous layer was extracted three times, each time with 30 ml. of ethyl acetate. The extracts were combined with the organic layer and the mixture was washed with ice water, dried over anhydrous magnesium sulfate, and concentrated under a reduced pressure to provide 2.0 g. of crude 9α-hydroxy-20-methoxy-16-methyl-11α,15-bis(tetrahydropyran-2-yloxy)-5(cis)-13(trans)prostadienoic acid. The crude product was applied to a silica gel column chromatography and developed using a mixture of ethyl acetate and n-hexane eluting solution to provide, 0.8031 g. of the aimed product showing $[\alpha]_D^{25}+39.5°$ (c=1.03, chloroform).

(e). In 5 ml. of ether was dissolved 140.6 mg. of 9α-hydroxy-20-methoxy-16-methyl-11α,15-bis(tetrahydropyran-2-yloxy)-5(cis)-13(trans)prostadienoic acid and the solution formed was cooled to 0° C. to −5° C. Then, 5.0 ml. of the solution (which was prepared in portion of 2.0 g. of anhydrous chromic acid, 9.65 g. of manganese sulfate hydrate, 2.13 ml. of concentrated sulfuric acid and water to make the whole volume 50 ml. and precooled to 0° C. to −5° C.) was added to the mixture followed by stirring for 3 hours at the same temperature.

After the reaction was over, 10 ml. of water was added to the reaction mixture and the mixture was extracted three times, each time with 30 ml. of ether. The extracts were combined, washed with water, dried over anhydrous magnesium sulfate, and concentrated under a reduced pressure to provide 120.5 mg. of 20-methoxy-16-methyl-9-oxo-11α,15-bis(tetrahydropyran-2-yloxy)-5(cis)-13(trans)prostadienoic acid.

EXAMPLE 1

In 5 ml. of a mixture of acetic acid, water, and tetrahyrofuran (19:11:3 by volume ratio) was dissolved 122.3 mg. of the 9α-hydroxy-20-methoxy-16-methyl-11α,15-bis(tetrahdropyran-2-yloxy)-5(cis)-13(trans)-prostadienoic acid prepared in Reference example 1-(f) and the solution was stirred for 3 hours at 40° C.±2° C.

After the reaction was over, the solvents were distilled off from the reaction mixture under a reduced pressure and the residue obtained was applied to a silica gel column chromatography and developed using a mixture of ethyl acetate and n-hexane as eluting solution to provide 45.3 mg. of 9α,11α,15-trihydroxy-20-methoxy-16-methyl-5(cis)-13(trans)prostadienoic acid showing $[\alpha]_D^{25}+26.3°$ (c=0.56, methanol).

EXAMPLE 2

In 5 ml. of a mixture of acetic acid, water, and tetrahydrofuran (19:11:3 by volume ratio) was dissolved 80.2 mg. of the 9α-hydroxy-20-methoxy-16-methyl-11α,15-bis(tetrahydrofuran-2-yloxy)-5(cis)-13(trans)prostadienoic acid prepared in Reference example 2-(d) and the solution was stirred for 3 hours at 40° C.±2° C. Then, by treating the reaction mixture obtained by the same manner as in Example 1, 29.3 mg. of 9α,11α,15(R)-trihydroxy-20-methoxy-16-methyl-5(cis)-13(trans)prostadienoic acid was obtained.

$[\alpha]_D^{25}+13.0°$ (c=0.37, methanol).

EXAMPLE 3

In 7 ml. of the mixture of acetic acid, water, and tetrahydrofuran (19:11:3 by volume ratio) was dissolved 143.5 mg. of the 20-methoxy-16-methyl-9-oxo-11α,15-bis(tetrahydropyran-2-yloxy)-5(cis)-13(trans)prostadienoic acid prepared in Reference example 1-(g) and the solution was stirred for 3 hours at 40° C.±2° C.

After the reaction was over, the solvents were distilled off from the reaction mixture under a reduced pressure and the residue obtained was applied to a silica gel column chromatography and developed using a mixture of ethyl acetate and n-hexane as eluting solution to provide 67.8 mg. of 11α,15-dihydroxy-20-metoxy-16-methyl-9-oxo-5(cis)-13(trans)prostadienoic acid showing $[\alpha]_D^{25}-51.5°$ (c=0.78, methanol).

EXAMPLE 4

In 7 ml. of a mixture of acetic acid, water, and tetrahydrofuran (19:11:3 by volume ratio) was dissolved 120.5 mg. of the 20-methoxy-16-methyl-9-oxo-11α,15(R)-bis(tetrahydropyran-2-yloxy)-5(cis)-13(trans)prostadienoic acid prepared in Reference Example 2-(e) and the solution was stirred for 3 hours at 40° C.±2° C. Then, by treating the reaction mixture obtained by the same manner as in Example 3, 59.7 mg of 11α,15-dihydroxy-20-methoxy-16-methyl-9-oxo-5(cis)-13(trans)prostadienoic acid showing $[\alpha]_D^{25}$ −60.2° (c=0.82, methanol) was obtained.

REFERENCE EXAMPLE 3

In 40 ml. of dry dimethoxyethane was suspended 555 mg. of 50% oily sodium hydride and after adding to the suspension a solution of 3.074 g. of dimethyl(7-methoxy-3-methyl-2-oxo)heptyl phosphonate showing $[\alpha]_D^{24}$ −13.8° (c=2.45, chloroform) in 20 ml. of dry dimethoxyethane at room temperature in nitrogen stream, the mixture was stirred for about one hour until the evolution of hydrogen gas ceased. Then, a solution of 4.1 g. of 4β-formyl-2-oxo-5α-p-phenylbenzyloxy-3aα,4α,5β,6aα-hexahydro-2H-cyclopenta[b]furan in 70 ml. of dry tetrahydrofuran was added to the mixture and the resultant mixture was further stirred for 90 minutes at room temperature.

After the reaction was over, dry ice powder, 250 ml. of methylene chloride, and 200 ml. of water were added to the reaction mixture and after shaking the mixture, the aqueous layer formed was separated from the organic solvent layer. The aqueous layer was extracted 4 times each time with 40 ml. of methylene chloride and the extracts were combined, washed with water, and dried. Then, the solvent was distilled off from the mixture under a reduced pressure and the residue formed was applied to a silica gel column chromatography and then developed using a mixture of ethyl acetate and n-hexane (1:1 by volume ratio) as eluting solution to provide 4.692 g. of colorless oily product of 4β-[8-methoxy-4-methyl-3-oxo-1-(trans)octenyl]-2-oxo-5αp-phenylbenzoyloxy-3aα,4α,5β,6aα-hexahydro-2H-cyclopenta-[b]furan showing $[\alpha]_D^{25}$ −118° (c=3.8, chloroform).

(b) To 260 ml. of dry ether were added 2.71 g. of sodium borohydride and 4.9 g. of anhydrous zinc chloride and after stirring the mixture at room temperature for 1.5 hours, a solution of 4.69 g. of the 4β-[8-methoxy-4-methyl-3-oxo-1-(trans)octenyl]-2-oxo-5α-p-phenyl-benzoyl-oxy-3aα,4α,5β,6aα-hexahydro-2H-cyclopenta[b]furan obtained in above step (a) in 75 ml. of dry dimethoxyethane was added to the mixture followed by stirring for 2 hours at room temperature.

After the reaction was over, 50 ml. of ice water was added gradually to the reaction mixture and then 200 ml. of water was further added to the mixture followed by shaking. Thereafter, the aqueous layer was separated from the organic layer. The aqueous layer was extracted five times each time with 50 ml. of ether and the extracts were combined, washed with water, and dried. Then, the solvent was distilled off from the mixture obtained under a reduced pressure and the residue obtained was applied to a silica gel column chromatography and developed using a mixture of ether and n-hexane (3:1 by volume ratio) as eluting solution to provide 2.219 g. of 4β-[3-hydroxy-8-methoxy-4-methyl-1-(trans-)octenyl]-2-oxo-5α-p-phenylbenzoyloxy-3aα,4α,5β,-6aα-hexahydro-2H-cyclopenta[b]furan showing $[\alpha]_D^{26}$ −83° (c=1.5, chloroform). Then, 0.783 g. of the 3-hydroxy compound of the aimed product showing $[\alpha]_D^{27}$ −91° (c=1.25, chloroform) and 1.175 g. of a mixture of the both products were obtained.

(c) To 120 of dry methanol were added 2.21 g. of the 4β-[3-hydroxy-8-methoxy-4-methyl-1-(trans)octenyl]-2-oxo-5α-p-phenylbenzoyloxy-3aα,4α,5β,6aα-hexahydro-2H-cyclopenta[b]furan showing $[\alpha]_D^{26}$ −83° (c=1.5, chloroform) obtained in above step (b) and 315 mg. of anhydrous potassium carbonate followed by stirring for 5 hours at room temperature. Then, the reaction mixture was neutralized with acetic acid and the solvent was distilled off under a reduced pressure. The residue formed was mixed with 250 ml. of ether and 50 ml. of water followed by shaking and the resultant mixture formed was separated into an aqueous layer and an organic layer. The aqueous layer was extracted twice each time with 40 ml. of ether. The extracts were combined with the organic layer. The mixture was washed with water, dried, and the solvent was distilled off under a reduced pressure. The residue obtained was applied to a silica gel column chromatography and developed using chloroform as eluting solution to remove methyl p-phenylbenzoate. Then, by developing using a mixture of methanol and chloroform (1:4 by volume ratio) as an eluting solution, 629 mg. of oily 4β-[3-hydroxy-8-methoxy-4-methyl-1-(trans)octenyl]-5α-hydroxy-2-oxo-3aα,4α,5β,6aα-hexahydro-2H-cyclopenta[b]furan showing $[\alpha]_D^{25}$ +7.1° (c=1.6, chloroform) was obtained.

(d) In 20 ml. of dry methylene chloride was dissolved 629 mg. of the 4β-[3-hydroxy-8-methoxy-4(R)-methyl-1-(trans)octenyl]-2-oxo-5α-hydroxy-2-oxo-3aα,4α,5β,-6aα-hexahydro-2H-cyclopenta[b]furan obtained in above step (c) and after adding to the solution 510 mg. of 2,3-dihyropyran and 15 mg. of p-toluenesulfonic acid monohydrate, the mixture was stirred for 15 minutes at room temperature.

Then, the reaction mixture was washed twice with diluted aqueous sodium bicarbonate and then with water, dried, and the solvent was distilled off under a reduced pressure. The residue obtained was applied to a silica gel column chromatography and developed using a mixture of ether and n-hexane (1:1, by volume ratio) as eluting solution to provide 864 mg. of oily 4β-[8-methoxy-4(R)-methyl-3-(tetrahydropyran-2-yloxy)-1-(trans)octenyl]-2-oxo-5β-(tetrahydropyran-2-yloxy)-3aα,4α,5β,6aα-hexahydro-2H-cyclopenta[b]furan showing $[\alpha]_D^{27}$ −27.4° (c=1.75, chloroform).

(e) In 40 ml. of dry toluene was dissolved 458 mg. of the 4β-[8-methoxy-4(R)-methyl-3-(tetrahydropyran-2-yloxy)-1-(trans)-octenyl]-2-oxo-5α-(tetrahydropyran-2-yloxy)-3aα,4α,5β,6aα-hexahydro-2H-cyclopenta[b]furan obtained in step (d) and after cooling the solution to −60° C. under a stream of nitrogen, 2.1 ml. of a toluene solution containing 205 mg. of diisobutylaluminum hydride followed by stirring for 30 minutes. Then, to the reaction mixture thus obtained were added 0.5 ml. of ethyl acetate, 0.5 ml. of methanol, and 2 ml. of water successively at the same temperature as above followed by shaking. Then, after filtering off the white precipitates formed, the filtrate layer was separated into an aqueous layer and an organic layer. The aqueous layer was extracted five times, each time with 30 ml. of benzene and the extracts were combined with the organic layer. After washing with water and drying, the solvent was distilled of f from the mixture under a reduced pressure to provide 404 mg. of colorless oily 4β-[8-methoxy-4-methyl-3-(tetrahydropyran-2-yloxy)-(trans)octenyl]-2-hydroxy-5α-(tetrahydropyran-2-yloxy)-3aα,4α,5β,6aα-hexahydro-2H-cyclopenta[b]furan.

(f) To 195 mg. of 50% oily sodium hydride was added 7 ml. of dry dimethylsulfoxide under a stream of nitrogen and the mixture was stirred under heating to 60° C. for about 1 hour until the evolution of hydrogen gas ceased. After cooling to room temperature, 930 mg. of 4-carboxybutyl triphenyl phosphonium bromide was added to the mixture and the to the clear red solution thus obtained was added a solution of 404 mg. of the 4β-[8-methoxy-4(R)-methyl-3-(tetrahydropyran-2-yloxy)-1-(trans)octenyl]-2-hydroxy-5α-(tetrahydropyran-2-yloxy)-3aα,4α,5β,6aα-hexahydro-2H-cyclopenta[b]furan obtained in above step (e) in 5 ml. of dry dimethyl sulfoxide followed by stirring for 2 hours at room temperature.

After the reaction was over, the reaction mixture was dispersed in 150 ml. of a mixture of ethyl acetate and ether (2:1 by volume ratio) saturated with dry ice and after adding thereto 70 ml. of ice water followed by shaking, the resultant mixture was separated into an aqueous layer and organic layer. The aqueous layer was extracted four times each time with 50 ml. of ethyl acetate and the extracts were combined with the organic layer. The mixture was washed with water, dried, and the solvents were distilled off under a reduced pressure. The residue obtinaed was applied to a silica gel column chromatography and developed using a mixture of ethyl acetate and n-hexane (1:2 by volume ratio) as eluting solution to provide 360 mg. of oily 9α-hydroxy-20-methoxy-16(R)-methyl-11α,15-bis(tetrahydropyran-2-yloxy)-5(cis)-13(trans)prostadienoic acid showing $[\alpha]_D^{23}+5.8°$ (c=1.25, chloroform).

(g) In 25 ml. of ether was dissolved 360 mg. of the 9α-hydroxy-20-methoxy-16(R)-methyl-11α,15-bis(tetrahydropyran-2-yloxy)-5(cis)-13(trans)prostadienoic acid obtained in above step, (f) and then to the solution was added slowly 11 ml. of a Jone's reagent (which was prepared in portion of 2.0 g. of anhydrous chromic acid, 9.65 g. of manganese sulfate hydrate, 2.13 ml. of concentrated sulfuric acid and water to make the whole volume 50 ml.) and precooled to 0° C. to −5° C.) followed by stirring for 90 minutes at the same temperature.

After the reaction was over, 50 ml. of ether and 40 ml. of saturated aqueous sodium sulfate solution were added to the reaction mixture followed by shaking and then the resultant mixture formed was separated into an queous layer and an organic layer. The aqueous layer was extracted four times each time with 40 ml. of ether and the extracts were combined with the organic layer. After washing the mixture with water and drying, the solvent was distilled off under a reduced pressure to provide 327 mg. of crude 20-methoxy-16-methyl-9-oxo-11α,15-bis(tetrahyropyran-2-yloxy)-5(cis)-13(trans)-prostadienoic acid.

REFERENCE EXAMPLE 4

(a) In 45 ml. of dry dimethoxyethane was suspended 528 mg. of 50% oily sodium hydride in nitrogen stream and after adding dropwise to the suspension a solution of 2.93 g. of dimethyl(7-methoxy-3(S)-methyl-2-oxo)-heptyl phosphanate showing $[\alpha]_D^{23}+12.8°$ (c=1, chloroform) in 20 ml. of dry dimethoxyethane, the mixture was stirred for 90 minutes at room temperature. Then, a solution of 4.04 g. of 4β-formyl-2-oxo-5α-p-phenylbenzoyloxy-3aα,4α,5β,6aα-hexahydro-2H-cyclopenta[b]-furan in 80 ml. of dry tetrahydrofuran was further added dropwise to the mixture and the resultant mixture was stirred for 90 minutes at room temperature. After the reaction was over, the reaction mixture was neutralized with a dry ice powder and after adding 150 ml. of water and saturating with sodium chloride, the resultant mixture was extracted four times each time with 50 ml. of methylene chloride. The extracts were combined, washed with water, dried over anhydrous magnesium sulfate and concentrated under a reduced pressure. The oily product obtained was applied to a silica gel column chromatography and developed using a mixture of ether and n-hexane (3:1 by volume ratio) as eluting solution to provide 3.3 g. of 4β-[8-methoxy-4-methyl-3-oxo-1-(trans)octenyl]-2-oxo-5α-p-phenylbenzoyloxy-3aα,5α,5β,6aα-hexahydro-2H-cyclopenta[b]furan-showing $[\alpha]_D^{23}-86.3°$ (c=1, chloroform).

(b) In 200 ml. of dry ether was suspended 1.65 g. of sodium borohydride and 2.98 g. of anhydrous zinc chloride and after stirring for 90 minutes at room temperature, a solution of 3.3 g. of 4β-[8-methoxy-4(S)-methyl-3-oxo-1-(trans)octenyl]-2-oxo-5α-p-phenylbenzoyloxy-3aα,4α,5β, 6aα-hexahydro-2H-cyclopenta[b]furan in 50 ml. of dry tetrahydrofuran was added dropwise to the suspension followed by stirring for 2 hours at room temperature.

After the reaction was over, the reaction mixture was neutralized with dry ice powder and after adding 150 ml. of water, the resultant mixture was extracted three times each time with 50 ml. of ether. The extracts were combined, washed with water, dried over anhydrous magnesium sulfate, and then concentrated under a reduced pressure to provide 2.8 g. of an oily product. Then, by applying the oily product to a silica gel column chromatography and developing using a mixture of ether and n-hexane (4:1 by volume ratio as eluting solution) 1.26 g. of 4β-[3-hydroxy-8-methoxy-4-methyl-1-(trans)octenyl]-2-oxo-5α-p-phenylbenzoyloxy-3aα,-4α,5β,6aα-hexahydro-2H-cyclopenta-[b]furan was obtained. $[\alpha]_D^{24}-126.1°$ (c=0.3, chloroform).

(c) In 40 ml. of dry methanol was dissolved 1.21 g. of the 4β-[3-hydroxy-8-metoxy-4-methyl-1-(trans)octenyl]-2-oxo-5α-p-phenylbenzoyl-oxy-3aα,4α,5β,6aα-hexahydro-2H-cyclopenta[b]furan obtained in above step (b) and after adding 169 mg. of anhydrous potassium carbonate to the solution, the mixture was stirred for 3 hours at room temperature. Then, the reaction mixture obtained was neutralized with 147 mg. of glacial acetic acid and methanol was distilled off under a reduced pressure. After adding 30 ml. of water to the residue obtained and saturating with sodium chloride, the mixture was extracted thrice each with 30 ml. of ether. The extracts were combined, washed with saturated aqueous sodium chloride solution, dried over anhydrous magnesium sulfate, and concentrated under a reduced pressure. The oily product thus obtained was applied to a silica gel column chromatography and developed using a mixture of chloroform and ethyl acetate (1:4 by volume ratio) as eluting solution to provide 651.7 mg. of 4β-[3-hydroxy-8-methoxy-4-methyl-1-(trans)octenyl]-5α-hydroxy-2-oxo-3aα,4α,5β,6aα-hexahydro-2H-cyclopenta[b]furan showing $[\alpha]_D^{23}$ −1.73° (c=1.2, chloroform).

(d) In 13 ml. of dry methylene chloride was dissolved 650 mg. of the 4β-[3(S)-hydroxy-8-methoxy-4-methyl-1-(trans)octenyl]-5α-hydroxy-2-oxo-3aα,4α,5β,6aα-hexahydro-2H-penta[b]furan obtained in step (c) and after adding to the solution 699 mg. of 2,3-dihydropyran and 4 mg. of p-toluenesulfonic acid monohydrate, the mixture was stirred for 30 minutes at room temperature.

After the reaction was over, 50 ml. of chloroform and 20 ml. of a diluted aqueous sodium bicarbonate solution were added to the reaction mixture followed by shaking. The organic layer formed was separated, washed with water, dried over anhydrous magnesium sulfate, and then the solvent was distilled off under a reduced pressure. The residue obtained was applied to a silica gel column chromatography and developed using a mixture of ether and n-hexane (1.2 by volume ratio) as eluting solution to provide 869 mg. of oily 4β-[8-methoxy-4-methyl-3(S)-(tetrahydropyran-2-yloxy)-1-(trans)octenyl]-2-oxo-5α-(tetrahydropyran-2-yloxy)-3aα,4α,5β,6aα-hexahydro-2H-cyclopenta[b]furan.

(e) In 40 ml. of dry toluene was dissolved 555 mg. of the 4β-[8-methoxy-(S)-methyl-3-(tetrahydropyran-2-yloxy)-1-(trans)-octenyl]-2-oxo-5α-(tetrahydropyra-2-yloxy)-3aα,4α,5β,6aα-hexahydro-2H-cyclopenta[b]furan obtained in step (d) in nitrogen stream and the solution was cooled to $-60°$ C. by dry ice-acetone. Then, 3.36 ml. of a toluene solution containing 328.3 mg. of diisobutylaluminum hydride was added dropwise to the solution in nitrogen stream and then the mixture was stirred for 30 minutes. Thereafter, 0.3 ml. of ethyl acetate and then 0.3 ml. of methanol were added successively to the mixture at the same temperature and after increasing the temperature upto room temperature, 50 ml. of water was added to the mixture, whereby white precipitates were formed. The precipitates were filtered off and the filtrate was separated into an aqueous layer and an organic layer. The aqueous layer was extracted twice each time with 50 ml. of benzene and the extracts were combined with the organic layer. The mixture was washed with saturated aqueous sodium chloride solution, dried over anhydrous magnesium sulfate, and concentrated under a reduced pressure at temperatures below room temperature to provide 492.2 mg. of 4β-[8-methoxy-4(S)-methyl-3-(tetrahydropyran-2-yloxy)-1-(trans)octenyl]-2-hydroxy-5α-(tetrahydropyran-2-yloxy)-3aα,4α,5β,6aα-hexahydro-2H-cyclopenta[b]furan.

(f) To 211.5 mg. of 50% oily sodium hydride was added 7 ml. of dry dimethyl sulfoxide in nitrogen stream and after heating the mixture to 60°-65° C., the mixture was stirred for about one hour until the evolution of hydrogen gas ceased. Then, the mixture was heated to room temperature and 1.01 g. of 4-carboxybutyltriphenyl phosphonium bromide was added to the mixture. Then, to the clear red solution thus obtained was added a solution of 442.9 mg. of the 4β-[8-methoxy-4-methyl-3-(tetrahydropyran-2-yloxy)-1-(trans)octenyl]-2-hydroxy-5α-(tetrahydropyran-2-yloxy)-3aα,4α,5β,6aα-hexahydro-2H-cyclopenta[b]furan obtained in step (e) in 5 ml. of dry dimethyl sulfoxide and the mixture was stirred for one hour at room temperature.

After the reaction was over, the reaction mixture was neutralized with a dry ice powder and then a mixture of 60 ml. of ether and 30 ml. of water saturated with dry ice was further added to the mixture. Then, the resultant mixture was separated into a aqueous layer and an organic layer and the aqueous layer was extracted thrice each with 30 ml. of ethyl acetate. The extracts were combined with the organic layer and the mixture was washed with ice water, dried over anhydrous magnesium sulfate, and concentrated under a reduced pressure. The residue obtained was applied to a silica gel column chromatography and developed using a mixture of ethyl acetate and n-hexane (1:1 by volume ratio) as eluting solution to provide 262 mg. of 9α-hydroxy-20-methoxy-16(S)-methyl-11α,15-bis(tetrahydropyran-2-yloxy)-5(cis)-13(trans)prostadienoic acid.

(g) In 7.7 ml. of ether was dissolved 262 mg. of the 9α-hydroxy-20-methoxy-16-methyl-11α,15-bis(tetrahdropyran-2-yloxy)-5(cis)-13(trans)prostadienoic acid obtained in step (f) and the solution was cooled to 0° C. to $-5°$ C. Then, 7.7 ml. of the solution (which was prepared in portion of 2.0 g. of anhydrous chromic acid 9.65 g. of manganese sulfate hydrate, and 2. 3 ml. of concentrated sulfuric acid and water to make the whole volume 50 ml. and precooled to 0° C. to $-5°$ C.) was added to the solution followed by stirring for 3 hours at the same temperature.

After the reaction was over, 10 ml. of water was added to the reaction mixture and then the mixture was extracted three times each time with 30 ml. of ether. The extracts were combined, washed with water, dried over anhydrous magnesium sulfate, and concentrated under a reduced pressure to provide 260 mg. of 20-methoxy-16(S)-methyl-9-oxo-11α,15-bis(tetrahydropyran-2-yloxy)-5(cis)-13(trans)-prostadienoic acid.

EXAMPLE 5

To 7 ml. of a mixture of acetic acid, water, and tetrahydrofuran (19:11:3 by volume ratio) was added 327 mg. of the 20-methoxy-16-methyl-9-oxo-11α,15-bis(tetrahydropyran-2-yloxy)-5(cis)-13(trans)prostadienoic acid prepared in Reference Example 3 and the solution was stirred for 2 hours at 40° C. After the reaction was over, the solvent was distilled off from the reaction mixture under a reduced pressure and the residue obtained was applied to a silica gel column chromatography and then developed using ethyl acetate eluting solution to provide 179 mg. of colorless oily 11α,15-dihydroxy-20-methoxy-16(R)-methyl-9-oxo-5(cis)-13(trans)-prostadienoic acid showing $[\alpha]_D^{25}$ $-58.5°$ (c=1.5, chloroform).

EXAMPLE 6

In 4 ml. of a mixture of acetic acid, water, and tetrahydrofuran (19:11:3 by volume ratio) was dissolved 260 mg. of the 20-methoxy-16-methyl-9-oxo-11α,15-bis(tetrahydropyran-2-yloxy)-5(cis)-13(trans)prostadienoic acid obtained in Reference Example 4 and the solution was stirred for 3 hours at 40° C.

After the reaction was over, the solvent was distilled off from the reaction mixture under a reduced pressure and the residue obtained was applied to a silica gel column chromatography and developed using ethyl acetate as eluting solution to provide 119.2 mg. of 11α,15-dihydroxy-20-methoxy-16-methyl-9-oxo-5(cis)-13(trans)-prostadienoic acid showing $[\alpha]_D^{25}$ $-65.0°$ (c=0.5, chloroform).

What is claimed is:

1. A pharmaceutical composition comprising an antiasthmatic effective amount of a 20-alkoxy-16-alkylprostadienoic acid derivative shown by the formula:

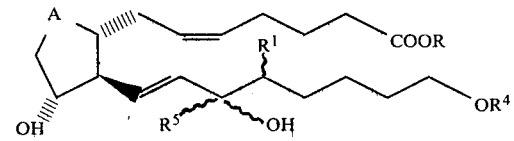

wherein A represents

R and $R^5$, which may be the same or different, each represents a hydrogen atom or a lower alkyl group, and $R^1$ and $R^4$, which may be the same or different, each represents a lower alkyl group and the pharmacologically acceptable nontoxic salts thereof as the active ingredient, and a therapeutically acceptable inert pharmaceutical carrier.

2. A pharmaceutical composition comprising an antiasthmatic effective amount of a 20-Alkoxy-16 alkyl-prostadienoic acid derivative shown by the formula:

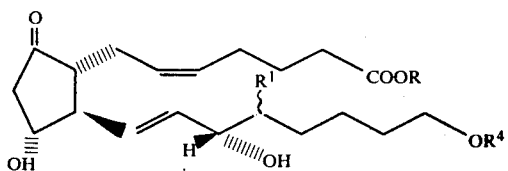

wherein R represents a hydrogen atom or a lower alkyl group and $R^1$ and $R^4$, which may be the same or different, each represents a lower alkyl group and the pharmacologically acceptable non-toxic salts thereof as the active ingredient, and a therapeutically acceptable inert pharmaceutical carrier.

3. A composition as claimed in claim 1 comprising 11α, 15(S)-dihydroxy-20-methoxy-16-methyl-9-oxo-5(cis)-13(trans)prostadienoic acid and the pharmacologically acceptable salts thereof as the active ingredient.

4. A composition as claimed in claim 1 comprising 11α, 15(S)-dihydroxy-20-methoxy-16-methyl-9-oxo-5(cis)-13(trans)prostadienoic acid methyl ester as the active ingredient.

* * * * *